United States Patent [19]

Hanatani et al.

[11] Patent Number: 5,246,808
[45] Date of Patent: Sep. 21, 1993

[54] HYDRAZONE COMPOUND AND PHOTOSENSITIVE MATERIAL USING SAID COMPOUND

[75] Inventors: Yasuyuki Hanatani, Sakai; Hiroaki Iwasaki, Hirakata, both of Japan

[73] Assignee: Mita Industrial Co., Ltd., Osaka, Japan

[21] Appl. No.: 850,991

[22] Filed: Mar. 12, 1992

[30] Foreign Application Priority Data

Mar. 19, 1991 [JP] Japan .................................. 3-55031
Mar. 19, 1991 [JP] Japan .................................. 3-55032

[51] Int. Cl.$^5$ ...................... G03G 5/06; G03G 15/04; G03G 15/02; C07C 251/86
[52] U.S. Cl. .......................................... 430/59; 430/69; 430/73; 430/74; 549/59; 549/74; 549/435; 549/442; 564/251
[58] Field of Search .................... 564/251; 430/59, 69, 430/73, 74; 549/59, 74, 435, 442

[56] References Cited

U.S. PATENT DOCUMENTS

| | | | |
|---|---|---|---|
| 4,465,857 | 8/1984 | Neumann et al. | 564/251 |
| 4,606,988 | 8/1986 | Sasaki | 430/59 |
| 4,666,809 | 5/1987 | Matsumoto et al. | 430/76 |
| 4,988,596 | 2/1990 | Ueda | 430/59 |

FOREIGN PATENT DOCUMENTS

| | | |
|---|---|---|
| 0084147 | 7/1983 | European Pat. Off. . |
| 0392805 | 10/1990 | European Pat. Off. . |
| 58-131954 | 8/1983 | Japan . |
| 1-298364 | 12/1989 | Japan . |
| 2-210451 | 8/1990 | Japan . |

Primary Examiner—Richard L. Raymond
Assistant Examiner—Peter G. O'Sullivan
Attorney, Agent, or Firm—Beveridge, DeGrandi, Weilacher & Young

[57] ABSTRACT

The present invention provides a hydrazone compound of the following general formula (I). This compound presents a higher hole mobility as compared with a conventional electric charge transferring material such as a conventional hydrazone compound or the like. Accordingly, when a photosensitive layer contains, as the electric charge transferring material, the hydrazone compound of the present invention, there can be obtained an electrophotosensitive material which is excellent in sensitivity and charging ability and has high repeating characteristics.

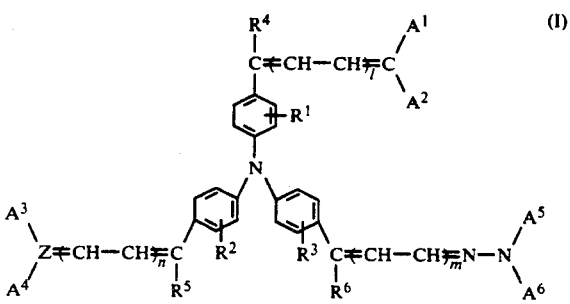

(wherein $R^1$, $R^2$, $R^3$, $R^4$, $R^5$ and $R^6$ may be same as or different from one another, and each is a hydrogen atom, an alkyl group, an alkoxy group, an aralkyl group or an aryl group, each of said alkyl, alkoxy, aralkyl and aryl groups may have a substituent group; $A^1$, $A^2$, $A^3$, $A^4$, $A^5$ and $A^6$ may be same as or different from one another, and each is a hydrogen atom, an alkyl group, an aralkyl group, an aryl group or a heterocyclic group, and each of said alkyl, aralkyl, aryl and heterocyclic groups may have a substituent group; l, m and n each is 0 or 1; Z is a group:N-N or a carbon atom; and provided that $A^1$, $A^2$, $A^3$, $A^4$, $A^5$ and $A^6$ should not be hydrogen atoms simultaneously.)

2 Claims, No Drawings

HYDRAZONE COMPOUND AND PHOTOSENSITIVE MATERIAL USING SAID COMPOUND

BACKGROUND OF THE INVENTION

The present invention relates to a hydrazone compound and a photosensitive material using such a compound.

As an electrophotosensitive material in an image forming apparatus such as an electrophotographic copying apparatus, a printer, a facsimile or the like, there is recently widely used an organic photosensitive material which is excellent in machinability and advantageous in production cost and which offers a great degree of freedom for design of performance.

For forming a copied image with the use of an electrophotosensitive material, the Carlson process is widely used. The Carlson process comprises the steps of uniformly charging a photosensitive material with electricity by corona discharge, exposing the charged photosensitive material to a document image, thereby to form an electrostatic latent image corresponding to the document image, developing the electrostatic latent image by a toner-containing developer, thereby to form a toner image, transferring the toner image to a medium such as paper, fixing the toner image transferred to the medium, and cleaning the photosensitive material to remove toner remaining thereon after the toner image has been transferred. To form an image of high quality in the Carlson process, it is required that the electrophotosensitive material is excellent in charging and photosensitive characteristics and presents a low residual potential after exposed to light.

As examples of the electrophotosensitive material, there are conventionally known inorganic photoconductive materials such as selenium, cadmium sulfide and the like. However, such materials are disadvantageous in view of toxicity and high production cost.

Accordingly, there are proposed so-called organic electrophotosensitive materials using organic materials instead of the inorganic materials. Each of the organic electrophotosensitive materials has a photosensitive layer comprising an electric charge generating material adapted to generate an electric charge upon exposure to light, and an electric charge transferring material for transferring an electric charge generated.

To satisfy a variety of requirements necessary for the organic electrophotosensitive material, it is required to properly select the electric charge generating material and the electric charge transferring material. As examples of the electric charge transferring material, a variety of organic compounds are proposed and put on the market. For example, there are known hydrazone compounds disclosed by Japanese Patent Unexamined Applications 131954/1983, 298364/1989 and 210451/1990.

However, these conventional electric charge transferring materials are poor in sensitivity and repeating characteristics.

SUMMARY OF THE INVENTION

It is an object of the present invention to provide a hydrazone compound suitable for the electric charge transferring material.

It is another object of the present invention to provide an electrophotosensitive material having high sensitivity and excellent in repeating characteristics.

The hydrazone compound according to the present invention is represented by the following general formula (I):

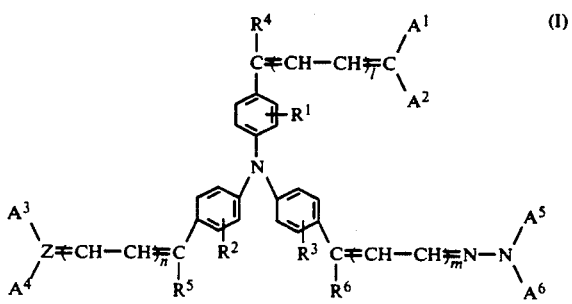

(wherein $R^1$, $R^2$, $R^3$, $R^4$, $R^5$ and $R^6$ may be same as or different from one another, and each is a hydrogen atom, an alkyl group, an alkoxy group, an aralkyl group or an aryl group, each of the alkyl, alkoxy, aralkyl and aryl groups may have a substituent group; $A^1$, $A^2$, $A^3$, $A^4$, $A^5$ and $A^6$ may be same as or different from one another, and each is a hydrogen atom, an alkyl group, an aralkyl group, an aryl group or a heterocyclic group, and each of the alkyl, aralkyl, aryl and heterocyclic groups may have a substituent group; l, m and n each is 0 or 1; Z is a group:N-N or a carbon atom; and provided that $A^1$, $A^2$, $A^3$, $A^4$, $A^5$ and $A^6$ should not be hydrogen atoms simultaneously.)

The hydrazone compound (1) of the present invention is effective as an electric charge transferring material, particularly as a hole transferring material, and presents a high hole mobility as compared with an electric charge transferring material of a conventional hydrazone compound.

More specifically, the hydrazone compound of the present invention includes the following formulas (I-a) and (I-b):

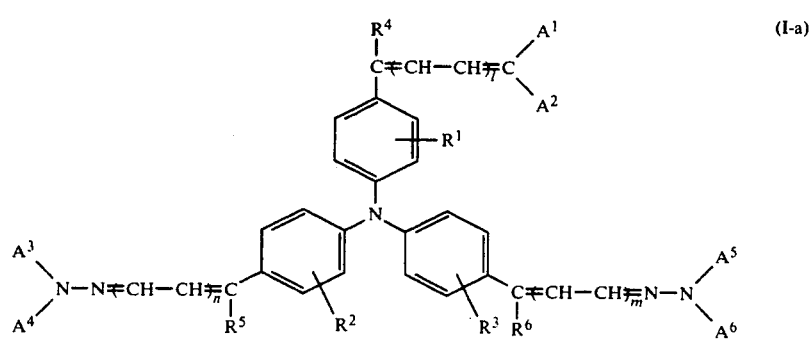

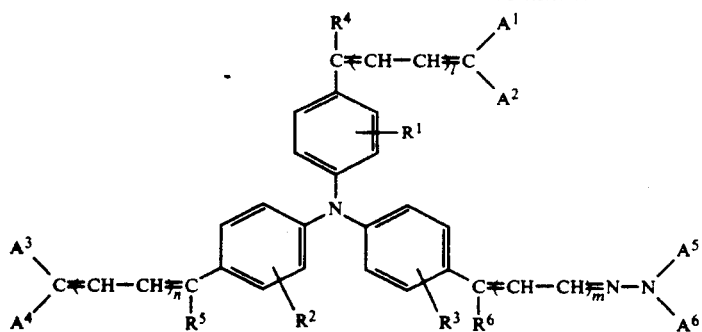

(I-b)

(wherein each of $R^1$, $R^2$, $R^3$, $R^4$, $R^5$, $R^6$, $A^1$, $A^2$, $A^3$, $A^4$, $A^5$, $A^6$, l, m and n is the same as defined above).

The photosensitive material containing the hydrazone compounds (I-a) and (I-b) is excellent in sensitivity and charging ability and presents high repeating characteristics.

DETAILED DESCRIPTION OF THE INVENTION

Examples of the alkyl group include methyl, ethyl, propyl, isopropyl, butyl, isobutyl, tert-butyl, pentyl and hexyl groups.

Examples of the alkoxy group include methoxy, ethoxy, isopropoxy, butoxy, t-butoxy and hexyloxy groups.

Examples of the aryl group include phenyl, naphthyl, anthryl and phenanthryl groups.

Examples of the aralkyl group include benzyl, α-phenethyl, β-phenetyl, 3-phenylpropyl, benzhydryl and trityl groups.

Examples of the heterocyclic group include thienyl, pyrrolyl, pyrrolidinyl, oxazolyl, isooxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino and thiazolyl groups.

Examples of the substituting group which may be to any of the groups above-mentioned, include a halogen atom, an amino group, a hydroxyl group, a carboxyl group which may be esterified, a cyano group, a straight-chain or branched alkyl group having 1 to 6 carbon atoms, a straight-chain or branched alkoxy group having 1 to 6 carbon atoms, and alkenyl group which may have an aryl group and which has 2 to 6 carbon atoms. Two or more substituting groups may be substituted, and two substituting groups may form a ring.

$A^1$ together with $A^2$, or $A^3$ together with $A^4$ may form a ring. An example of such a ring includes carbazole.

Specific examples of the hydrazone compound of the general formula (I-a) include the following ones.

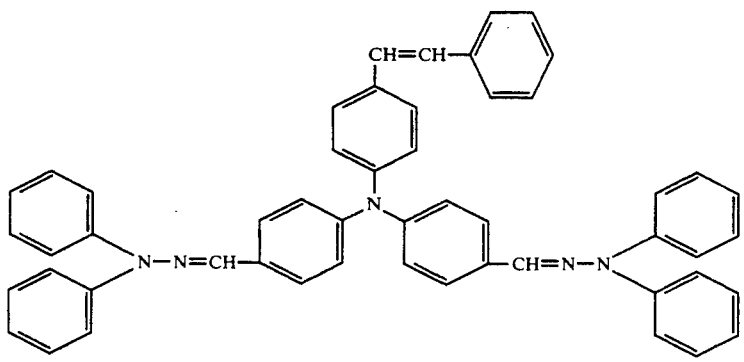

(2)

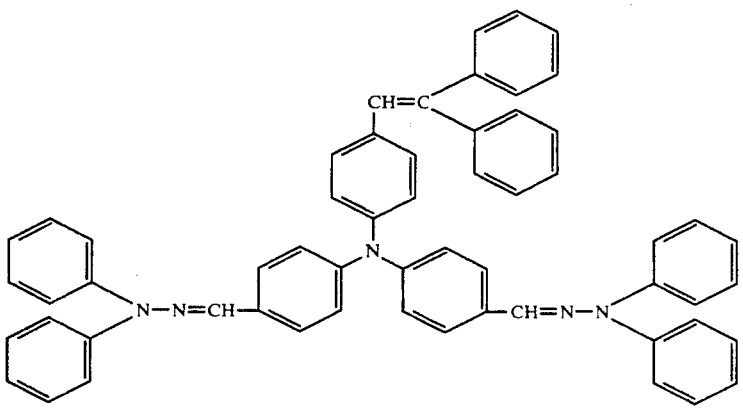

(3)

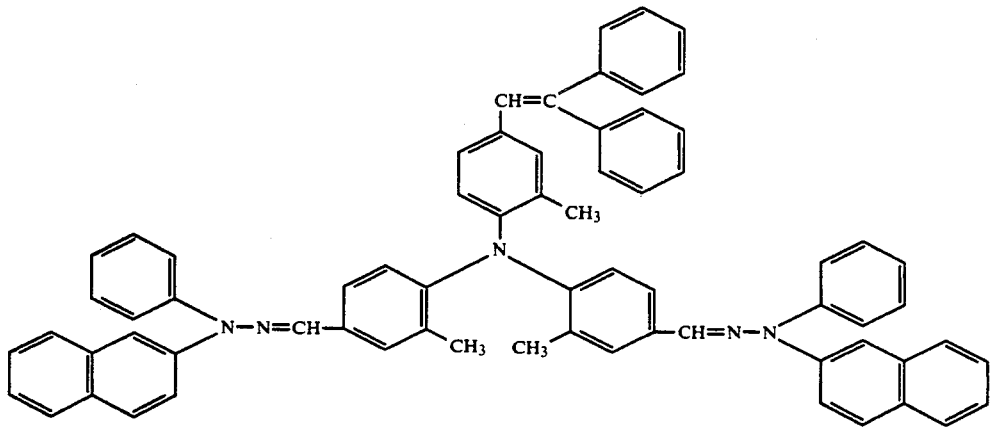
(4)
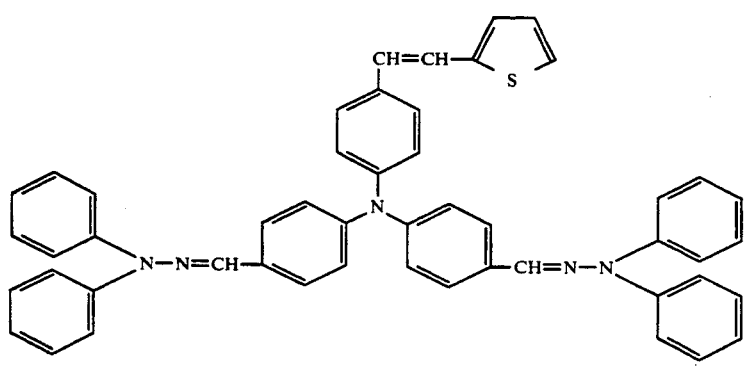
(5)
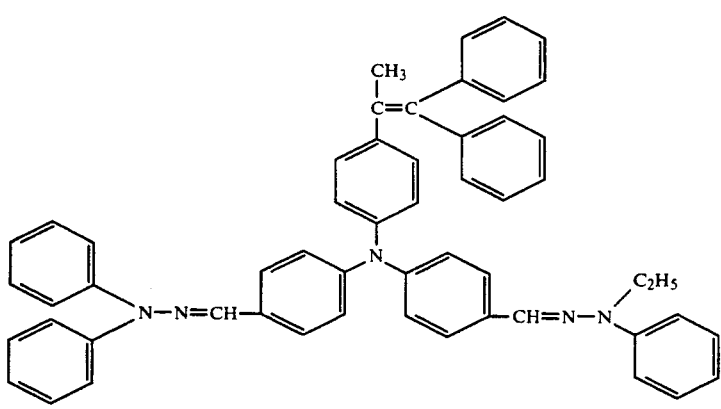
(6)
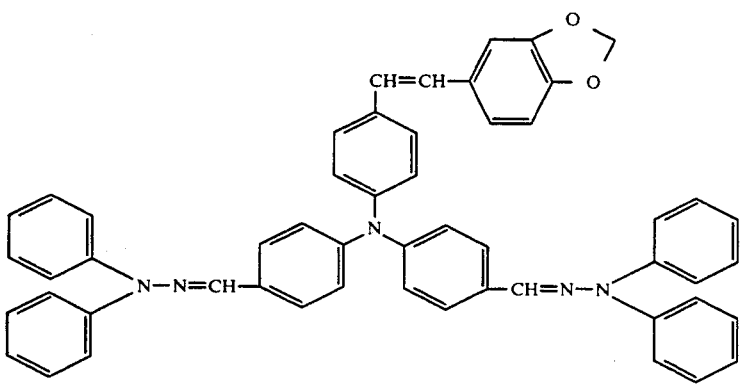
(7)

-continued
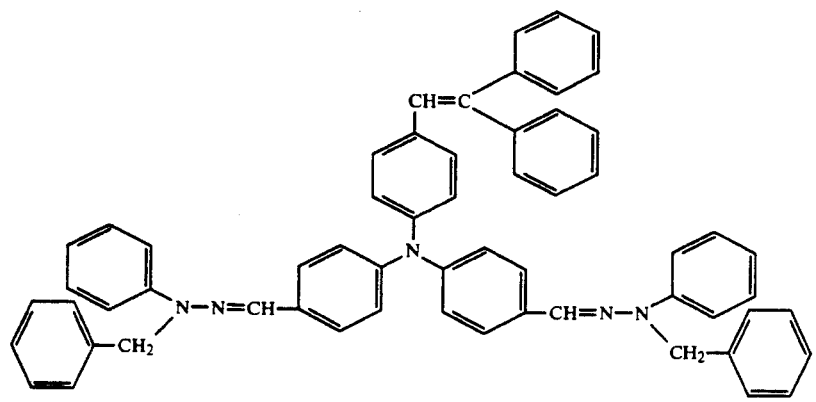
(8)
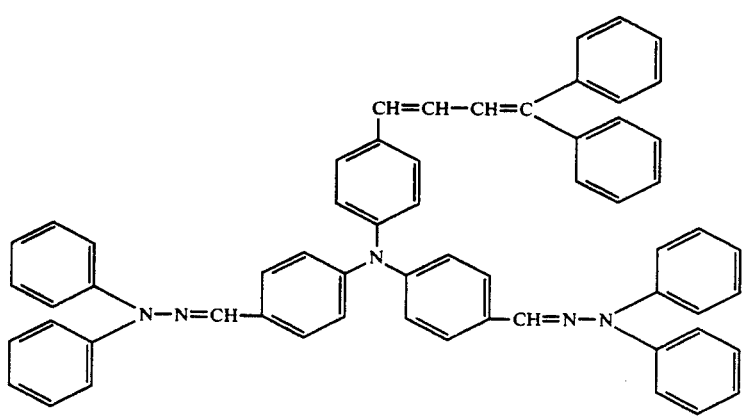
(9)
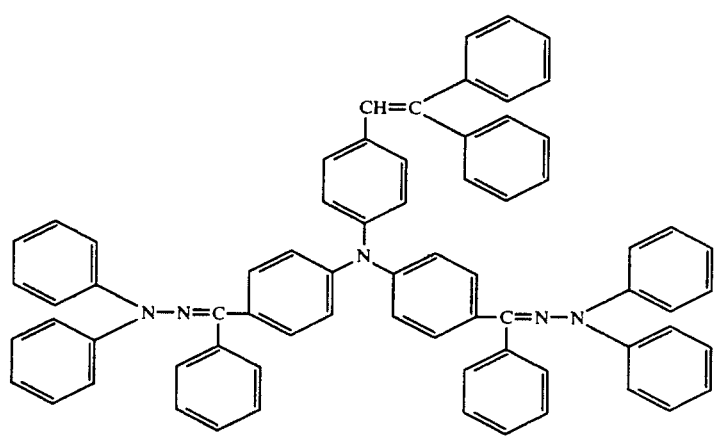
(10)
The compound of the general formula (I-a) may be produced by the following reaction formula for example:

Reaction Formula:

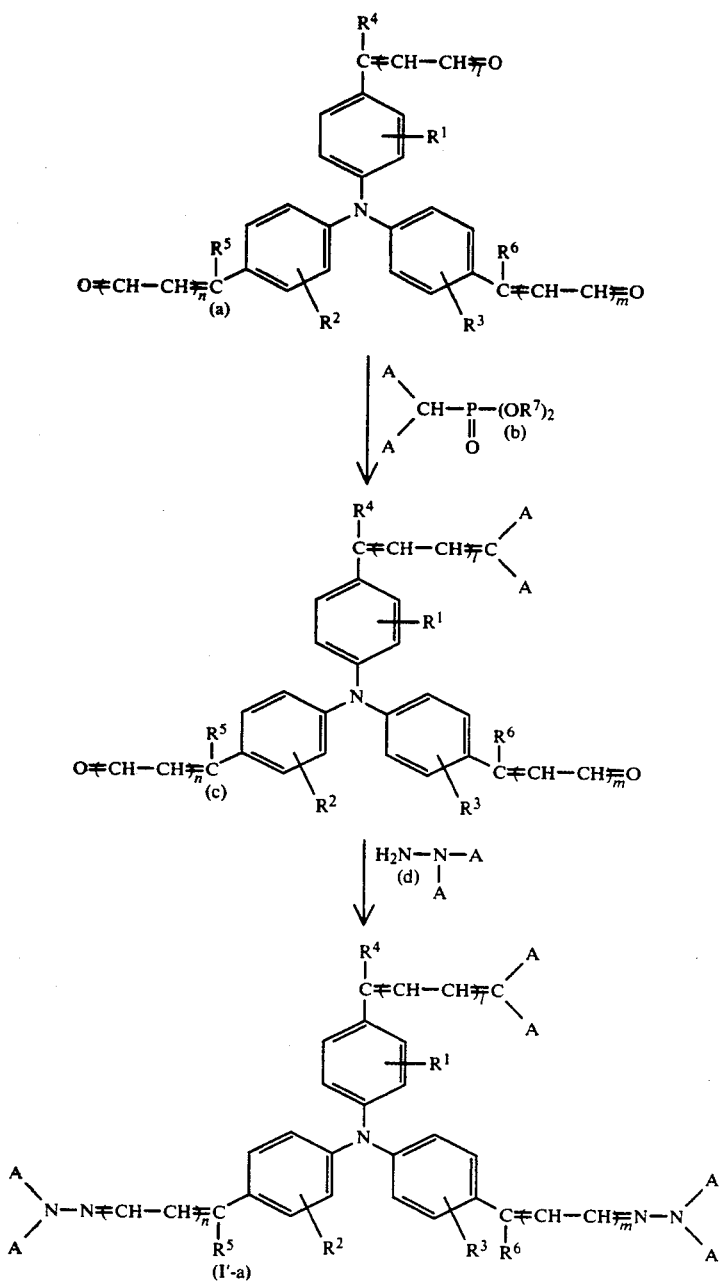

(wherein each of $R^1$, $R^2$, $R^3$, $R^4$, $R^5$, $R^6$, l, m and n is the same as defined above, and each A is any of $A^1$, $A^2$, $A^3$, $A^4$, $A^5$, $A^6$; and $R^7$ is a lower alkyl group).

More specifically, a compound of the formula (b) is reacted in an equimolar amount with an aldehyde compound of the formula (a) under the presence of base (sodium hydroxide, potassium hydroxide or the like), thereby to prepare an intermediate represented by a formula (c) having a stillbene structure. The reaction is carried out in a solvent at a temperature from 0° to 120° C. As the solvent, there may be used, for example, dimethylformamide, dimethyl sulfoxide, N-methylpyrrolidone or the like. Then, the intermediate compound (c) thus prepared is reacted with a hydrazine compound represented by a formula (d) under acid conditions with acetic acid or the like added, thereby to prepare a compound (I'-a) of the present invention. In the reaction, the hydrazine compound (d) is used in a double molar amount with respect to the compound (c). This reaction can be conducted at a temperature from room temperature to 120° C. in a solvent similar to that above-mentioned. This reaction proceeds quickly and almost quantitatively.

Specific examples of the hydrazone compound represented by the general formula (I-b) include the following ones.

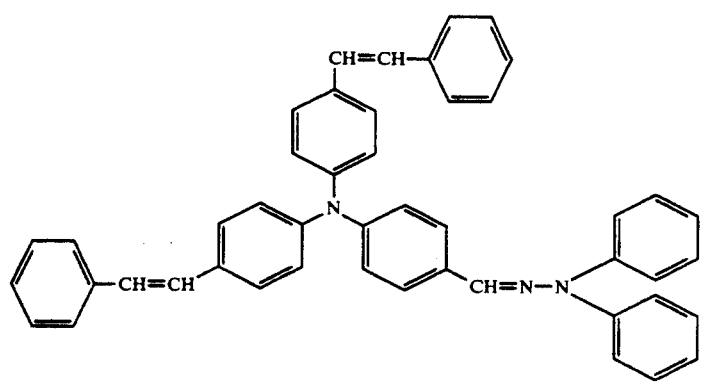
(12)
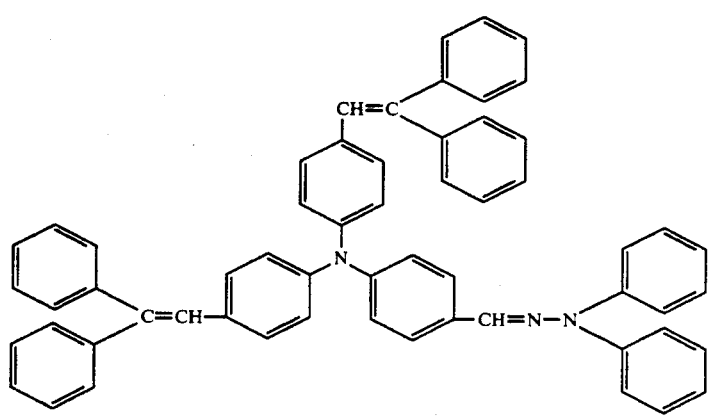
(13)
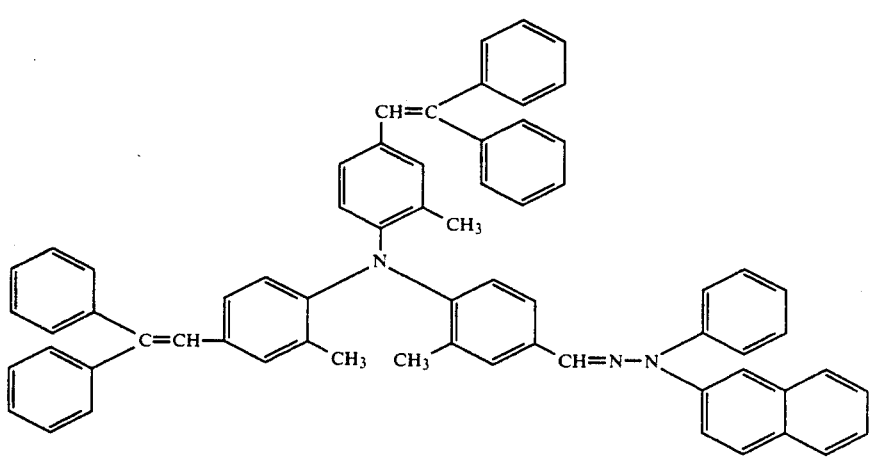
(14)
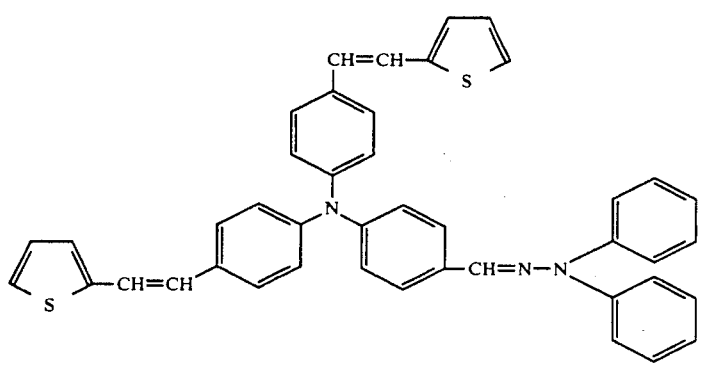
(15)

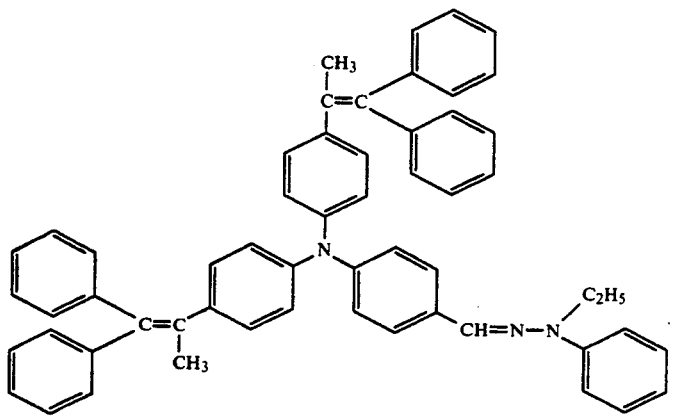
(16)
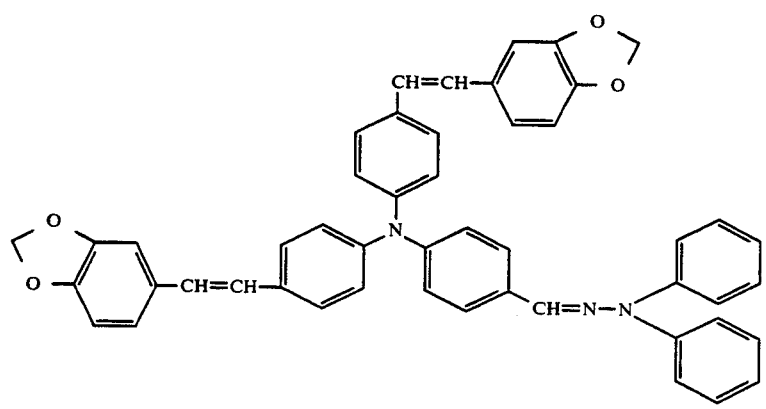
(17)
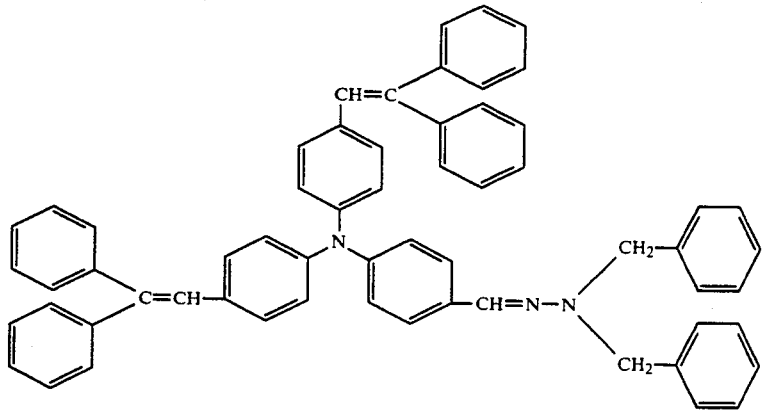
(18)
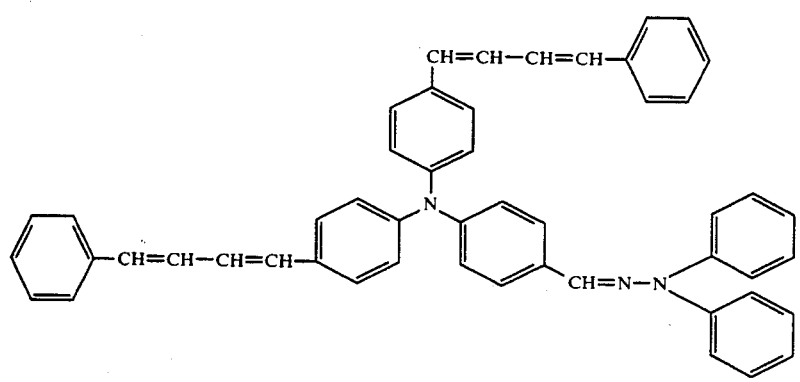
(19)

(20)
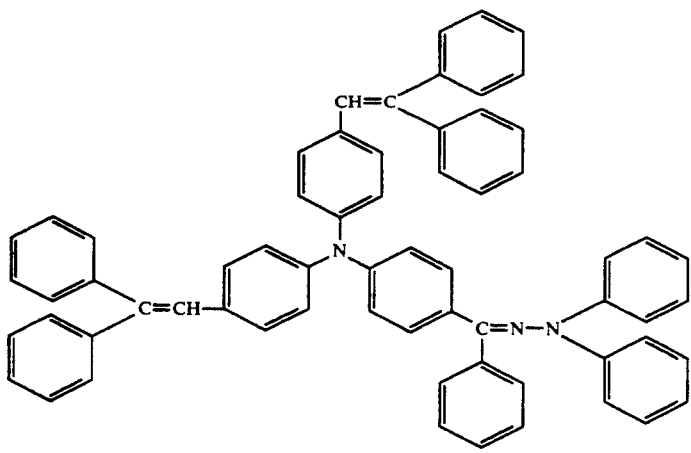
The compound of the general formula (I-b) may be produced by the following reaction formula for example:
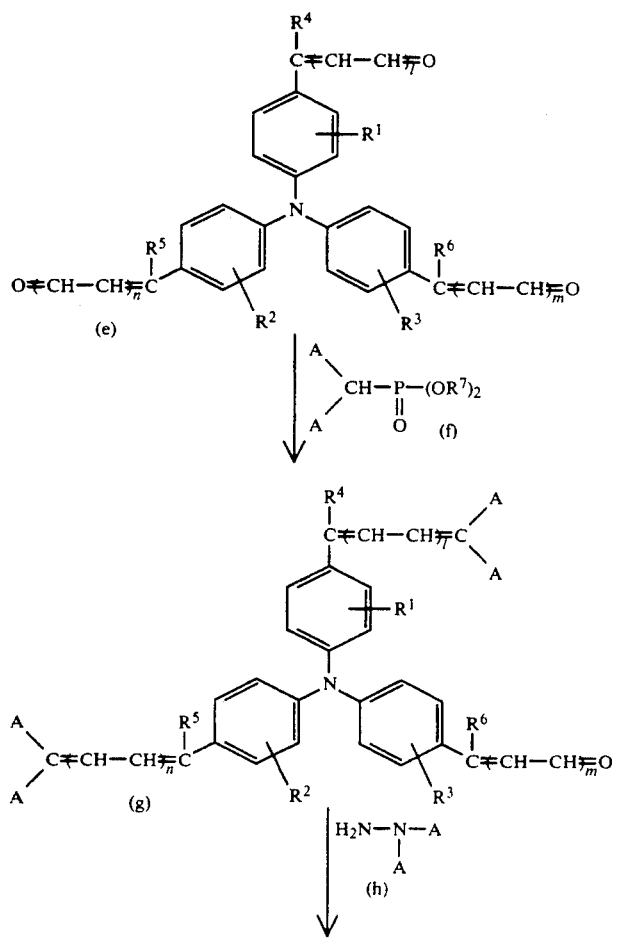

Reaction Formula:

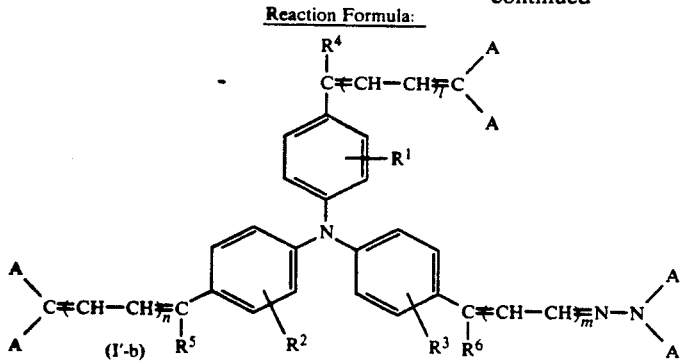

(wherein each of A, $R^1$, $R^2$, $R^3$, $R^4$, $R^5$, $R^6$, $R^7$, l, m and n is the same as defined above).

More specifically, under the presence of base (sodium hydroxide, potassium hydroxide or the like), a compound of the general formula (f) is reacted in a double molar amount with an aldehyde compound of the general formula (e) in which two out of three aldehyde groups are reacted, thereby to prepare an intermediate represented by a formula (g) having a stillbene structure. The reaction is carried out in a solvent at a temperature from 0° to 120° C. As the solvent, there may be used, for example, dimethylformamide, dimethyl sulfoxide, N-methylpyrrolidone or the like. Then, the intermediate compound (g) thus prepared is reacted with a hydrazine compound of the formula (h) under acid conditions with acetic acid or the like added, thereby to prepare a compound (I'-b) of the present invention. In the reaction, the hydrazine compound (h) is used in an equimolar amount with respect to the compound (g). This reaction can be conducted at a temperature from room temperature to 120° C. in a solvent similar to that above-mentioned. This reaction proceeds quickly and almost quantitatively.

The compound of the general formula (I) in accordance with the present invention may be contained in a binding resin, alone or in combination with other conventional electric charge transferring material, thereby to form a photosensitive layer. Examples of the conventional electric charge transferring material include nitrogen-containing cyclic compounds and condensated polycyclic compounds which include oxadiazole compounds such as 2,5-di(4-methylaminophenyl)-1,3,4-oxadiazole and the like, styryl compounds such as 9-(4-diethylaminostyryl) anthracene and the like, carbazole compounds such as polyvinyl carbazole and the like, pyrazoline compounds such as 1-phenyl-3-(p-dimethylaminophenyl)pyrazole and the like, triphenylamine compounds, indole compounds, oxazole compounds, isooxazole compounds, thiazole compounds, thiadiazole compounds, imidazole compounds, pyrazole compounds, triazole compounds and the like. These examples of the electric charge transferring material may be used alone or in combination of plural types. When there is used an electric charge transferring material having film-forming properties such as polyvinyl carbazole or the like, the binding resin is not necessarily required.

The compound of the general formula (I) may be applied to any of so-called single-layer type and multi-layer type photosensitive materials.

To form a single-layer type electrophotosensitive material, there may be formed, on a conductive substrate, a photosensitive layer containing the compound of the general formula (I) serving as the electric charge transferring material, an electric charge generating material, a binding resin and the like.

To form a multi-layer type electrophotosensitive material, an electric charge generating layer containing an electric charge generating material may be formed on a conductive substrate, and an electric charge transferring layer containing the compound of the general formula (I) serving as the electric charge transferring material may then be formed on the electric charge generating layer. By reversing the laminating order, the electric charge generating layer may be formed on the electric charge transferring layer.

Examples of the electric charge generating material include selenium, selenium-tellurium, seleniumarsenic, amorphous silicon, pyrylium salt, an azo compound, a disazo compound, a phthalocyanine compound, an anthanthrone compound, a perylene compound, an indigo compound, a triphenylmethane compound, a threne compound, a toluidine compound, a pyrazoline compound, a perylene compound, a quinacridon compound, a pyrrolopyrrole compound and the like. These examples may be used alone or in combination of plural types.

As the binding resin, any of a variety of resins may be used. Examples of the binding resin include: thermoplastic resins such as a styrene polymer, a styrene-butadiene copolymer, a styrene-acrylonitrile copolymer, a styrene-maleic acid copolymer, an acrylic polymer, a styrene-acrylic copolymer, polyethylene, an ethylene-vinyl acetate copolymer, chlorinated polyethylene, polyvinyl chloride, polypropylene, a vinyl chloride-vinyl acetate copolymer, polyester, alkyd resin, polyamide, polyurethane, polycarbonate, polyarylate, polysulfon, diarylphthalate resin, ketone resin, polyvinyl butyral resin, polyether resin and the like; crosslinking thermosetting resins such as silicone resin, epoxy resin and the like; photosetting resins such as epoxy-acrylate, urethane-acrylate and the like. These polymers may be used alone or in combination of plural types.

A solvent is used when the electric charge generating material, the electric charge transferring material and the binding resin are dissolved to form a coating solution. Examples of such a solvent include: alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, carbon tetrachloride, chlorobenzene and the like; ethers such as dimethyl ether, diethyl ether, tetrahydrofuran, ethylene glycol dimethyl ether, diethylene glycol dimethyl ether and the like; ketones such as acetone, methylethyl ketone, cyclohexanone and the like; esters such as ethyl acetate, methyl acetate and the like; dimethylformaldehyde; dimethylformamide; dimethylsulfoxide and the like. These solvents may be used alone or in combination of plural types.

To improve the electric charge generating layer in sensitivity, there may be used a conventional sensitizer such as tert-phenyl, halonaphtoquinone, acenaphthylene or the like, together with the electric charge generating material.

To improve the electric charge transferring and generating materials in dispersibility, applicability and the like, there may be used a surfactant, a levelling agent and the like.

Examples of the conductive substrate include: single metals, such as aluminium/copper, tin, platinum, silver, vanadium, molybdenum, chromium, cadmium, titanium, nickel, paradium, indium, stainless steel, brass and the like; plastic material vapor-deposited or laminated with any of the metals above-mentioned; glass material coated with aluminum iodide, tin oxide, indium oxide or the like.

The conductive substrate may be made in the form of a sheet, a drum or the like. The substrate itself may be conductive or only the surface of the substrate may be conductive. Preferably, the substrate has a sufficient mechanical strength when used.

In a multi-layer type photosensitive material, the electric charge generating material forming the electric charge generating layer, and the binding resin may be used at any of a variety of blending ratios. The electric charge generating material may be used preferably in a range from 5 to 500 parts by weight, and more preferably from 10 to 250 parts by weight, for 100 parts by weight of the binding resin.

The thickness of the electric charge generating layer is optional, but preferably in a range from about 0.01 to about 5 $\mu$m and more preferably from about 0.1 to about 3 pm.

The compound of the general formula (I) (the electric charge transferring material) forming the electric charge transferring layer, and the binding resin may be used at any of a variety of blending ratios. However, to facilitate the transmission of the electric charge generated in the electric charge generating layer by light irradiation, the compound of the general formula (I) may be used preferably in a range from 10 to 500 parts by weight, and more preferably from 25 to 200 parts by weight, for 100 parts by weight of the binding resin.

The thickness of the electric charge transferring layer is preferably in a range from about 2 to about 100 $\mu$m and more preferably from about 5 to about 30 $\mu$m.

In the single-layer type photosensitive material, the electric charge generating material may be used preferably in a range from 2 to 20 parts by weight, and more preferably from 3 to 15 parts by weight, for 100 parts by weight of the binding resin. Particularly, the compound of the general formula (I) (the electric charge transferring material) may be used preferably in a range from 40 to 200 parts by weight and more preferably from 50 to 150 parts by weight for 100 parts by weight of the binding resin. The thickness of the single-layer type photosensitive material is preferably from about 10 to about 50 $\mu$m and more preferably from about 15 to about 30 $\mu$m.

For forming the photosensitive layer containing the electric charge generating layer and the electric charge transferring layer by a coating method, a coating solution is prepared by mixing the electric charge generating material, the electric charge transferring material and the binding resin by a conventional method with the use of, for example, a roll mill, a ball mill, an atriter, a paint shaker, a supersonic dispenser or the like.

EXAMPLES

The following description will discuss in detail the present invention with reference to Examples and Comparative Examples.

Hydrazone Compound of General Formula (I-a)

(1) Synthesis Examples of Electric Charge Transferring Material

Example 1

Synthesis of Compound of Formula (2)

Under the presence of sodium hydroxide, 20.0 g of a compound of the following formula:

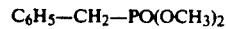

$$C_6H_5-CH_2-PO(OCH_3)_2$$

was reacted with 32.9 g of tri(4-formylphenyl)amine in dimethyl sulfoxide at 80° C. for 3 hours. The reaction product was isolated and refined by a conventional method, and then reacted with 6.0 g of diphenyl hydrazine $(C_6H_5)_2N-NH_2$ under acid conditions in ethyl alcohol at 60° C., thereby to prepare a compound of formula (2).

The following shows the results of elemental analysis of the compound.

In the form of $C_{46}H_{41}N_5$: Calculation value (%) C83.22, H6.23, N10.55; Measured value (%) C83.37, H6.16, N10.47;

With the use of suitable starting materials, the following compounds were prepared in the same manner as in Example 1.

Example 2

Compound of Formula (3)

The following shows the results of elemental analysis of the compound.

In the form of $C_{58}H_{45}N_5$: Calculation value (%) C85.79, H5.58, N8.63; Measured value (%) C85.66, H5.63, N8.71;

Example 3

Compound of Formula (4)

The following shows the results of elemental analysis of the compound.

In the form of $C_{69}H_{55}N_5$: Calculation value (%) C86.85, H5.81, N7.34; Measured value (%) C86.83, H5.78, N7.39;

Example 4

Compound of Formula (8)

The following shows the results of elemental analysis of the compound.

In the form of $C_{60}H_{49}N_5$: Calculation value (%) C85.78, H5.88, N8.34; Measured value (%) C85.83, H5.95, N8.22;

Example 5

Compound of Formula (9)

The following shows the results of elemental analysis of the compound.

In the form of $C_{60}H_{47}N_5$: Calculation value (%) C85.99, H5.65, N8.36; Measured value (%) C86.10, H5.61, N8.29;

Example 6

Compound of Formula (10)

The following shows the results of elemental analysis of the compound.

In the form of $C_{70}H_{53}N_5$: Calculation value (%) C87.19, H5.54, N7.27; Measured value (%) C87.12, H5.52, N7.36;

(2) Preparation of Electrophotosensitive Materials

Preparation of Multi-Layer Type Electrophotosensitive Materials

Examples 7 to 11 and Comparative Examples 1 to 3

First, 2 parts by weight of each of electric charge generating materials set forth in Tables 1 and 2, 1 part by weight of polyvinyl butyral resin ("S-lecBM-5" manufactured by Sekisui Kagaku Kogyo Co., Ltd.) and 120 parts by weight of tetrahydrofuran were dispersed for 2 hours with a paint shaker using zirconia beads (2 mm dia.). Each of the resulting dispersions was applied onto an aluminum sheet with the use of a wire bar and dried at 100° C. for 1 hour, thereby to prepare an electric charge generating layer of 0.5 μm. In Tables 1 and 2, A, B and C refer to the compounds represented by the following formulas (A), (B) and (C), respectively.

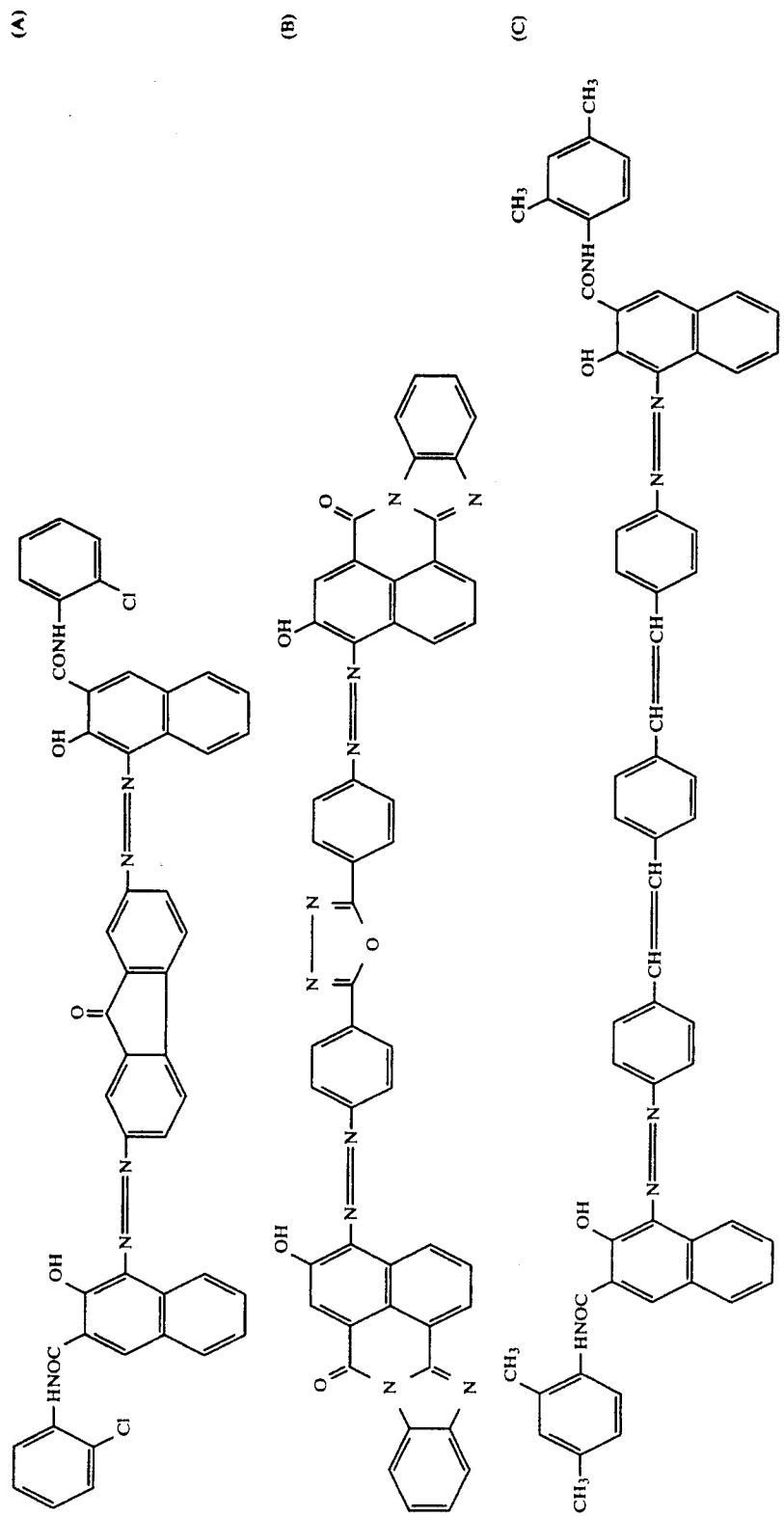

With the use of a wire bar, there was applied, onto each of the electric charge generating layers thus prepared, a solution in which 1 part by weight of each of electric charge transferring materials set forth in Tables 1 and 2, and 1 part by weight of polycarbonate resin ("Z-300" manufactured by Mitsubishi Gas Kagaku Co., Ltd.) were dissolved in 9 parts by weight of toluene. Each of the electric charge transferring materials was then dried at 100° C. for 1 hour to prepare an electric charge transferring layer of 22 μm. In Table 1, the electric charge transferring materials used in Examples 7 to 11 are shown by the Nos. of the compounds set forth in connection with Examples 1 to 7. In Table 2, the electric charge transferring materials X, Y, Z used in Comparative Examples 1 to 3 refer to compounds represented by the following formulas (X), (Y), (Z), respectively.

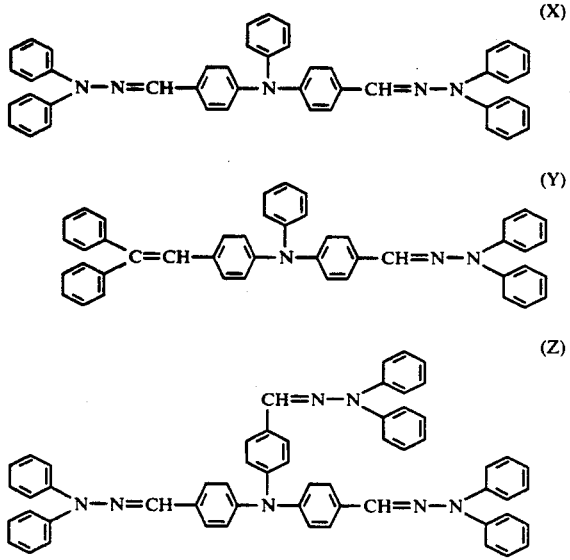

Preparation of Single-Layer Type Electrophotosensitive Materials

Examples 12 to 14 and Comparative Examples 4 to 6

One part by weight of each of the electric charge generating materials set forth in Tables 1 and 2, and 60 parts by weight of tetrahydrofuran were dispersed for 2 hours with a paint shaker using zirconia beads (2 mm dia.). Added to each of the resulting dispersions were (i) 50 parts by weight of a tetrahydrofuran solution containing a solid content of 20% by weight of polycarbonate resin ("Z-300" manufactured by Mitsubishi Gas Kagaku Co., Ltd.) and (ii) 10 parts by weight of each of the electric charge transferring materials set forth in Tables 1 and 2. Each of the resulting dispersions was further dispersed for 1 hour. Each of the resulting dispersions was applied onto an aluminum sheet with the use of a wire bar and dried at 100° C. for 1 hour, thereby to prepare a photosensitive layer of 20 μm. In Tables 1 and 2, the electric charge generating materials and the electric charge transferring materials used in Examples 12 to 14 and Comparative Examples 4 to 6 are shown by the marks and Nos. of the compounds in the same manner as in Examples 7 to 11 and Comparative Examples 1 to 3.

(3) Evaluation of Electrophotosensitive Materials

Each of the photosensitive materials of Examples and Comparative Examples above-mentioned was measured for surface potential, half-life light exposure amount ($E_{\frac{1}{2}}$) and residual potential with an evaluation testing device ("EPA$^{8100}$" manufactured by Kawaguchi Denki Co., Ltd.).

The measuring conditions are set forth below:
Light intensity: 50 lux
Exposure intensity: 1/15 second
Surface potential:

The value of the flowing current was adjusted such that the surface potential was in the vicinity of (+/−)700V.
Light source: Tungsten lamp
Destaticizer: 200 lux
Measurement of residual potential:

The measurement was started 0.2 second after light-exposure started.

Table 1 shows the test results of Examples 7 to 14, while Table 2 shows the test results of Comparative Examples 1 to 6.

TABLE 1

| Example | Charge Transferring Material | Charge Generating Material | Surface Potential (V) | $E_{\frac{1}{2}}$ (lux/sec) | Residual Potential (V) |
|---|---|---|---|---|---|
| 7 | 2 | A | −710 | 1.32 | −115 |
| 8 | 3 | A | −705 | 1.44 | −120 |
| 9 | 8 | A | −700 | 1.16 | −105 |
| 10 | 9 | B | −715 | 0.92 | −95 |
| 11 | 10 | C | −705 | 1.16 | −110 |
| 12 | 2 | A | +695 | 1.52 | +130 |
| 13 | 3 | A | +700 | 1.63 | +145 |
| 14 | 4 | A | +695 | 1.36 | +125 |

TABLE 2

| Comparative Example | Charge Transferring Material | Charge Generating Material | Surface Potential (V) | $E_{\frac{1}{2}}$ (lux/sec) | Residual Potential (V) |
|---|---|---|---|---|---|
| 1 | X | A | −715 | 5.32 | −190 |
| 2 | Y | A | −710 | 5.31 | −230 |
| 3 | Z | A | −700 | 4.32 | −195 |
| 4 | X | A | +710 | 5.12 | +250 |
| 5 | Y | A | +695 | 5.52 | +300 |
| 6 | Z | A | +705 | 4.81 | +265 |

From the test results above-mentioned, it is found that the photosensitive layers of Examples 7 to do not present substantial difference in surface potential from the photosensitive layers of Comparative Examples 1 to 6, but are superior in half-life light exposure and residual potential and remarkably improved in sensitivity.

Hydrazone Compound of General Formula (I-b)

(1) Synthesis Examples of Electric Charge Transferring Materials

Synthesis of Compound of Formula (12)

Under the presence of sodium hydroxide, 40.0 g of a compound of the following formula:

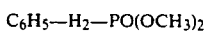

was reacted with 32.9 g of tri(4-formylphenyl)amine in dimethylformamide at 80° C. for 5 hours. The reaction product was isolated and refined by a conventional method, and then reacted with 3.0 g of diphenyl hydrazine $(C_6H_5)_2N-NH_2$ under acid conditions in ethyl alcohol at 60° C., thereby to prepare a compound of the formula (12).

The following shows the results of elemental analysis of the compound.

In the form of $C_{47}H_{27}N_3$: Calculation value (%) C87.68, H5.79, N6.53; Measured value (%) C87.74, H5.84, N6.42;

With the use of suitable starting materials, the following compounds were prepared in the same manner as in Example 15.

Example 16

Compound of Formula (13)

The following shows the results of elemental analysis of the compound.

In the form of $C_{59}H_{45}N_3$: Calculation value (%) C89.02, H5.70, N5.28; Measured value (%) C88.93, H5.75, N5.32;

Example 17

Compound of Formula (14)

The following shows the results of elemental analysis of the compound.

In the form of $C_{66}H_{53}N_3$: Calculation value (%) C89.25, H6.02, N4.73; Measured value (%) C89.32, H6.01, N4.81;

Example 18

Compound of Formula (18)

The following shows the results of elemental analysis of the compound.

In the form of $C_{61}H_{49}N_3$: Calculation value (%) C88.91, H5.99, N5.10; Measured value (%) C88.94, H6.04, N5.02;

Example 19

Compound of Formula (19)

The following shows the results of elemental analysis of the compound.

In the form of $C_{51}H_{41}N_3$: Calculation value (%) C88.02, H5.96, N6.04; Measured value (%) C88.07, H5.94, N6.01;

Example 20

Compound of Formula (20)

The following shows the results of elemental analysis of the compound.

In the form of $C_{65}H_{49}N_3$: Calculation value (%) C89.52, H5.66, N4.82; Measured value (%) C89.44, H5.69, N4.87;

(2) Preparation and Evaluation of Electrophotosensitive Materials

Examples 21 to 25

Multi-layer type electrophotosensitive materials were prepared in the same manner as in those using the hydrazone compound (I-a).

Examples 26 to 28

Single-layer type electrophotosensitive materials were prepared in the same manner as in those using the hydrazone compound (I-a).

Each of the photosensitive materials of Examples 21 to 28 was evaluated for surface potential, half-life light exposure and residual potential in the same manner mentioned earlier. The test results are shown in Table 3, in which the electric charge generating and transferring materials used are shown by the marks and Nos. of the compounds in the same manner as in Table 1.

TABLE 3

| Example | Charge Transferring Material | Charge Generating Material | Surface Potential (V) | $E_{\frac{1}{2}}$ (lux/sec) | Residual Potential (V) |
|---|---|---|---|---|---|
| 21 | 12 | A | −700 | 0.97 | −100 |
| 22 | 13 | A | −705 | 0.98 | −105 |
| 23 | 18 | A | −695 | 1.22 | −110 |
| 24 | 19 | B | −700 | 1.35 | −120 |
| 25 | 20 | C | −710 | 1.16 | −115 |
| 26 | 12 | A | +700 | 1.16 | +125 |
| 27 | 13 | A | +700 | 1.36 | +130 |
| 28 | 14 | A | +705 | 1.27 | +125 |

From the test results in Table 3, it is found that the photosensitive layers of Examples 21 to 28 do not present a substantial difference in surface potential from the photosensitive layers of Comparative Examples 1 to 6, but are superior in half-life light exposure and residual potential and remarkably improved in sensitivity.

What is claimed is:

1. A hydrazone compound represented by the following formula (I-a):

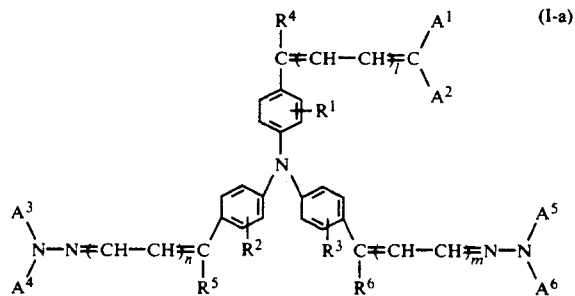

wherein each of $R^1$, $R^2$, $R^3$, $R^4$, $R^5$ and $R^6$ may be same as or different from one another, and each is a hydrogen atom, an alkyl group, an alkoxy group, an aralkyl group or an aryl group, wherein each of said alkyl, alkoxy, aralkyl and aryl groups may have a substituent group; wherein $A^1$, $A^2$, $A^3$, $A^4$, $A^5$ and $A^6$ may be the same as or different from one another, and each is a hydrogen atom, an alkyl group, an aralkyl group, an aryl group or a heterocyclic group, wherein each of said alkyl, aralkyl, aryl and heterocyclic groups may have a substituent group; and wherein l, m and n each is 0 or 1; and provided that $A^1$, $A^2$, $A^3$, $A^4$, $A^5$ and $A^6$ are not hydrogen atoms simultaneously.

2. A photosensitive material, comprising:
   a conductive substrate; and
   a photosensitive layer containing a hydrazone compound disposed on said conductive substrate,
   wherein the hydrazone compound is represented by the following formula (I-a):

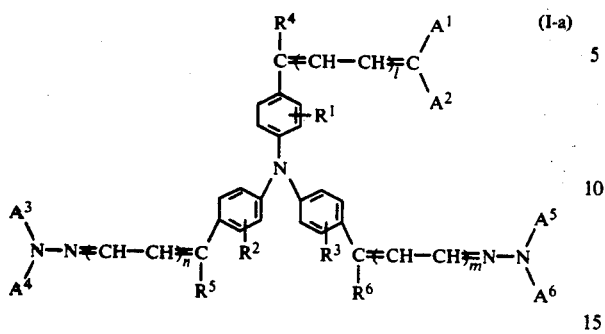

(I-a)

wherein each of $R^1$, $R^2$, $R^3$, $R^4$, $R^5$ and $R^6$ may be same as or different from one another, and each is a hydrogen atom, an alkyl group, an alkoxy group, an aralkyl group or an aryl group, wherein each of said alkyl, alkoxy, aralkyl and aryl groups may have a substituent group; wherein $A^1$, $A^2$, $A^3$, $A^4$, $A^5$ and $A^6$ may be the same as or different from one another, and each is a hydrogen atom, an alkyl group, an aralkyl group, an aryl group or a heterocyclic group, wherein each of said alkyl, aralkyl, aryl and heterocyclic groups may have a substituent group; and wherein l, m and n each is 0 or 1; and provided that $A^1$, $A^2$, $A^3$, $A^4$, $A^5$ and $A^6$ are not hydrogen atoms simultaneously.

* * * * *